Figure 1B:
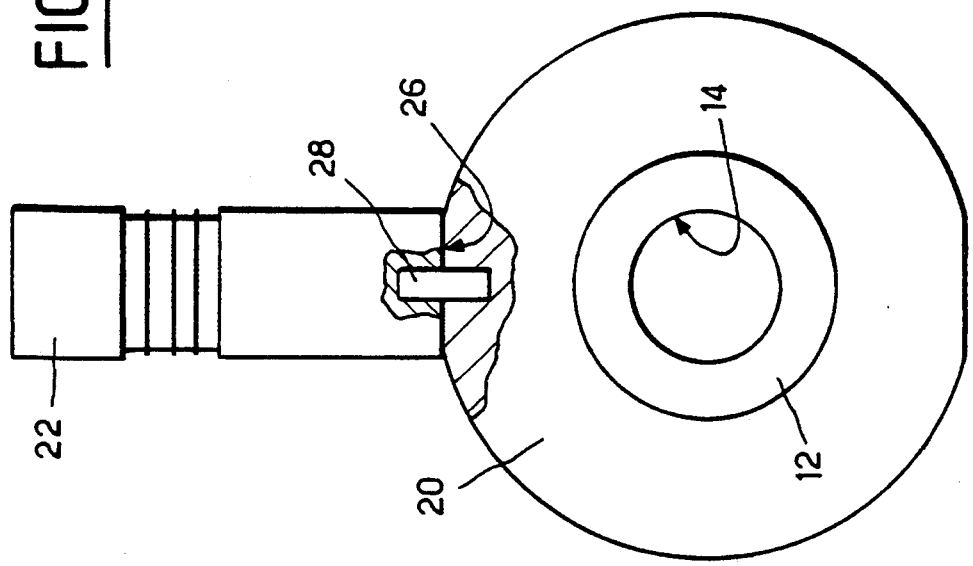

United States Patent [19]
Vaxelaire

[11] Patent Number: 5,384,508
[45] Date of Patent: Jan. 24, 1995

[54] MODULAR UNIT FOR A TUBULAR ULTRASONIC REACTOR

[76] Inventor: Philippe Vaxelaire, 6 rue Henri Jaccaz, 74100 Ville-La Grand, France

[21] Appl. No.: 90,133
[22] PCT Filed: Jan. 15, 1992
[86] PCT No.: PCT/FR92/00029
  § 371 Date: Jul. 19, 1993
  § 102(e) Date: Jul. 19, 1993
[87] PCT Pub. No.: WO82/00260
  PCT Pub. Date: Feb. 4, 1982

[30] Foreign Application Priority Data
Jan. 17, 1991 [FR] France .................. 91 00499

[51] Int. Cl.$^6$ ............................. H01L 41/08
[52] U.S. Cl. ..................... 310/334; 310/323
[58] Field of Search ............ 310/321, 323, 334, 328

[56] References Cited
U.S. PATENT DOCUMENTS

| | | | |
|---|---|---|---|
| 4,069,433 | 1/1978 | McShane | 310/325 |
| 4,074,152 | 2/1978 | Asai et al. | 310/334 |
| 4,392,380 | 7/1983 | Caines | 73/644 |
| 4,433,916 | 2/1984 | Hall | 310/334 |
| 4,808,084 | 2/1989 | Tsubouchi et al. | 310/328 |

FOREIGN PATENT DOCUMENTS

| | | |
|---|---|---|
| 2354827 | 1/1978 | France . |
| WO82/00260 | 2/1982 | WIPO . |
| WO82/03795 | 11/1982 | WIPO . |

OTHER PUBLICATIONS

Japanese Journal of Applied Physics, vol. 20 (1981), Supplement 20-3, pp. 169–172.

*Primary Examiner*—Thomas M. Dougherty
*Attorney, Agent, or Firm*—Jacobson, Price, Holman & Stern

[57] ABSTRACT

Modular reactor unit for continuous ultrasonic processing of substances and/or reagents, characterized in that it comprises a tubular metallic body having a cylindrical inner surface and a straight circular cross secton, open at its feed and discharge ends, in that the surface of said tubular metallic body has, in the region of its nodal zone, a radially projecting collar coaxial to said tube, and in that at least one ultrasonic converter is radially arranged integral with said collar at the periphery of the latter, the frequency of said converter being equal to the frequency of vibration of said collar and to the frequency of longitudinal vibration of said tubular metallic body.

11 Claims, 7 Drawing Sheets

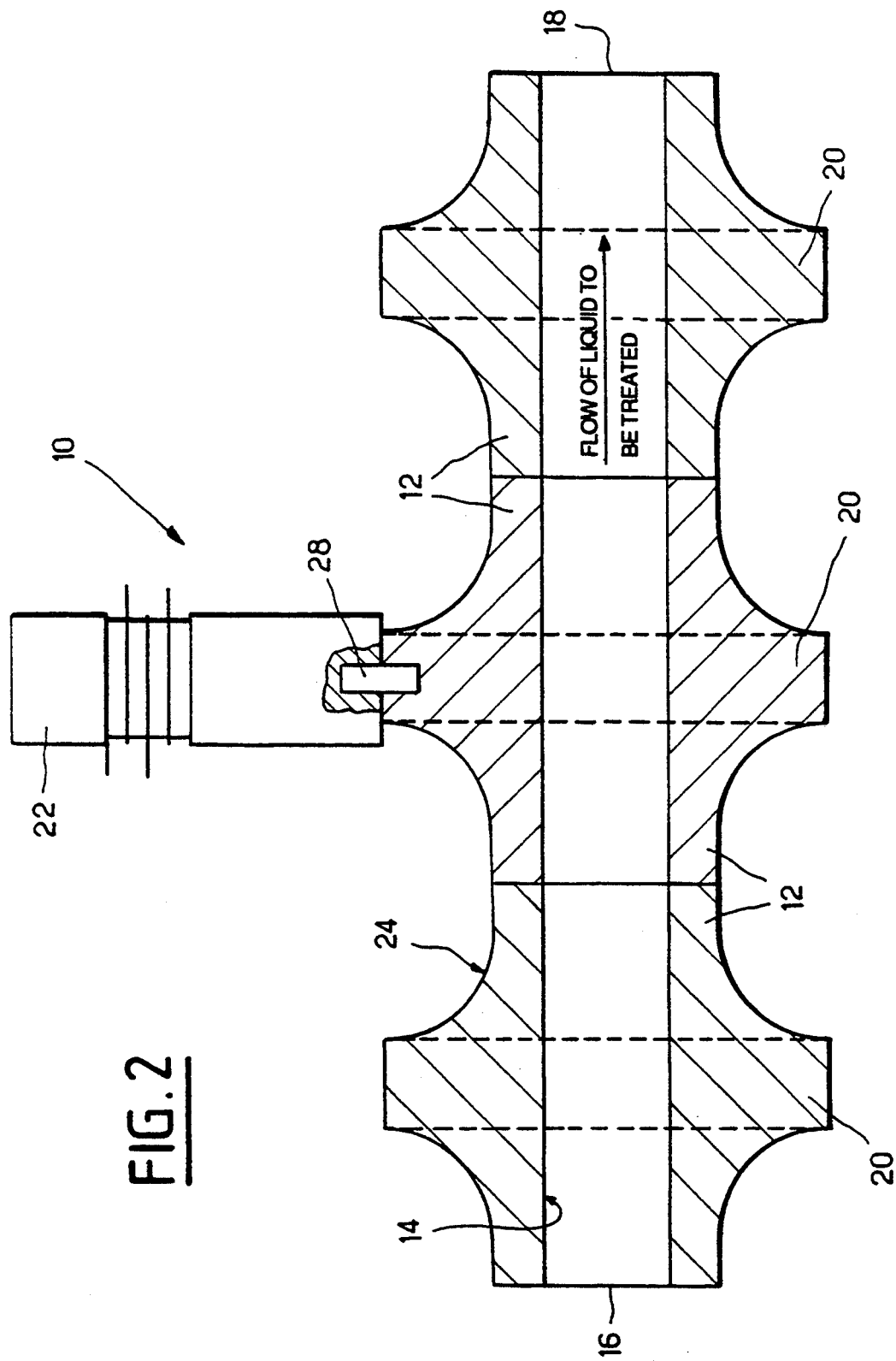

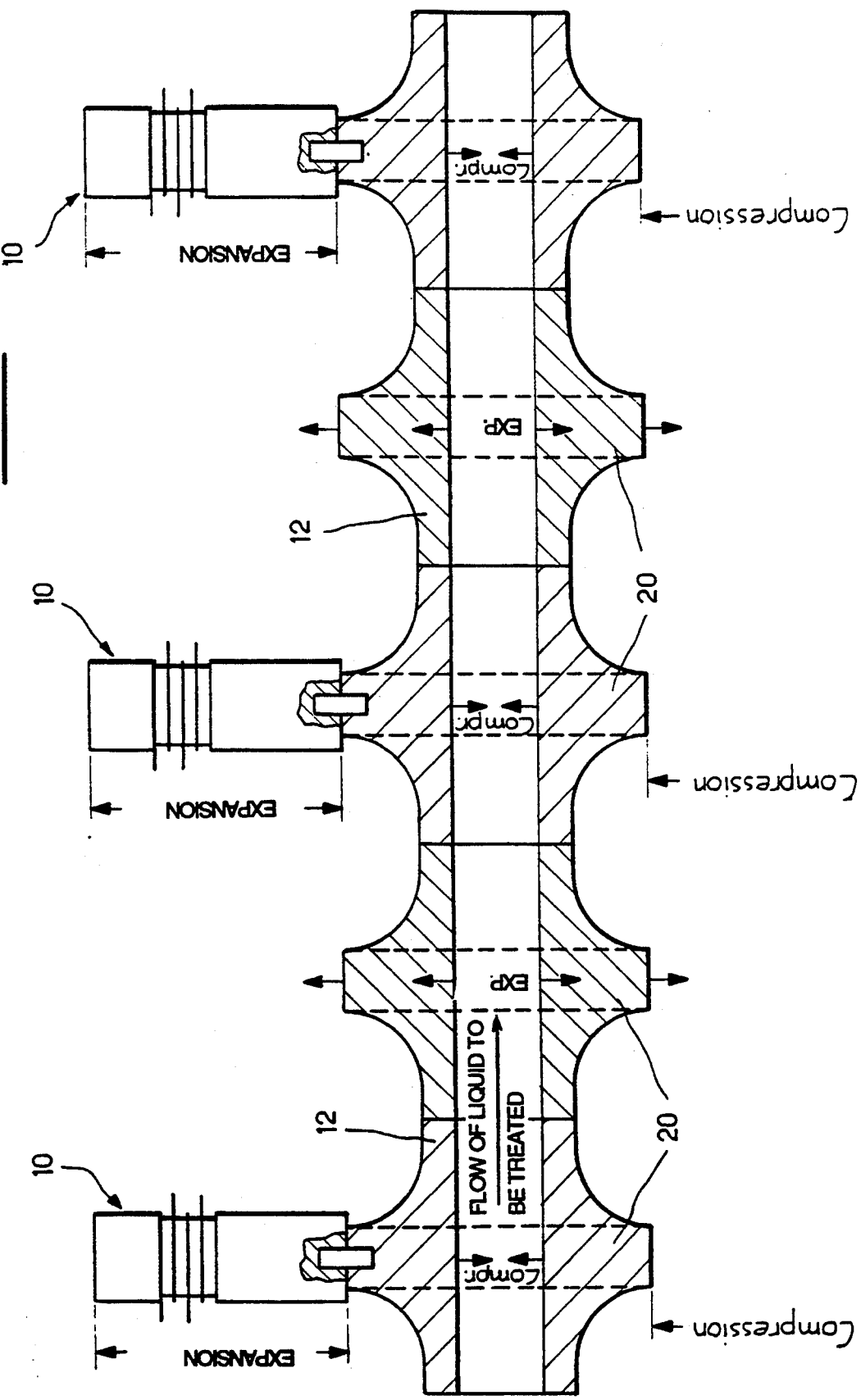

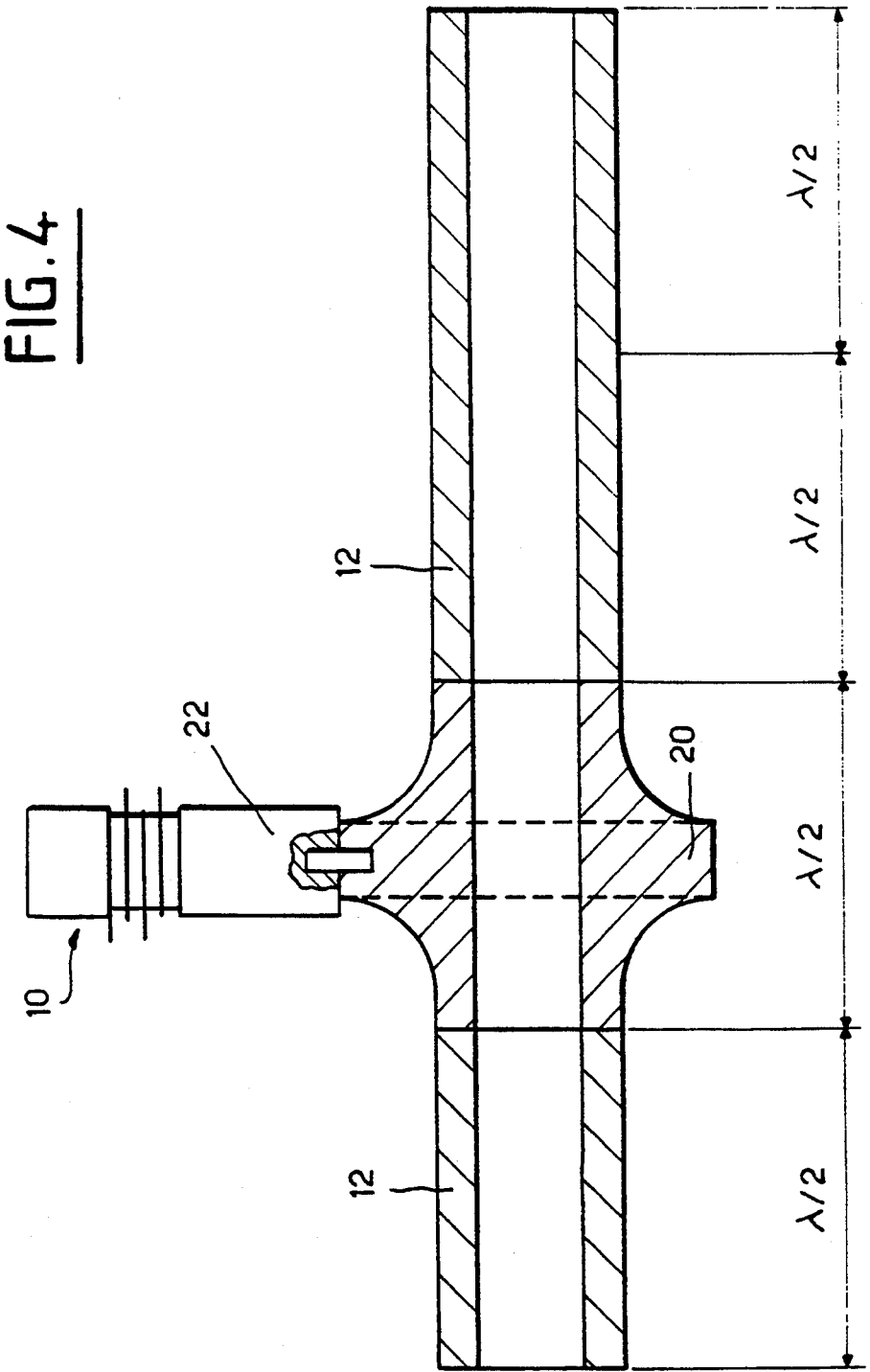

ically at most equal to one half-wavelength at said frequency.

MODULAR UNIT FOR A TUBULAR ULTRASONIC REACTOR

The present invention concerns a modular unit for a tubular ultrasonic reactor and various applications said unit in the form of multireactors adapted to various specific applications.

In the current state of the art various ultrasonic devices are known for treating liquids. These are mainly devices derived from the technology of ultrasonic cleaning and usually in the form of thin metal tanks with a plurality of emitters fixed to the bottom.

Vibrating the bottom of the tank induces cavitation in the liquid it contains, the intensity of such cavitation decreasing in the direction away from the source, i.e. the bottom of the tank.

Another known technique uses two diaphragms in opposition. Just as in the aforementioned cleaning technology, a number of emitters are disposed on two metal plates facing each other with a distance of between 1.5 and 4 mm, called the coupling distance, between them. The liquid to be treated is passed between the two emitter plates.

Another configuration uses a plurality of emitters fixed to the periphery of a metal tube. This configuration can be used to treat a liquid in motion but has the drawbacks of requiring a large number of emitters, of being unable to achieve amplitudes exceeding those routinely achieved by the cleaning technology and of requiring replacement of the entire system in the event of wear of the treatment tube in contact with the treated product.

All the known techniques are in fact equivalent to ultrasonic cleaning techniques in which emitters are fixed directly to metal diaphragms, tubes or tank bottoms.

Finally, there are ultrasonic probes for use in laboratory experiments of which well known examples are the Sonifier (BRANSON) and Vibracell (SONIC'S and MATERIALS). This type of equipment can treat small volumes or low flowrates.

An object of the present invention is to propose a tubular ultrasonic reactor using the principle of mechanical resonance to propagate ultrasonic vibration for treating fluid passing through said reactor coherently from a small number of emitters.

According to the present invention, this objective has been achieved by developing a modular reactor unit characterized in that it comprises a tubular metal body with a cylindrical inside surface and a circular transverse cross-section open at feed and discharge ends, in that the outside surface of said tubular metal body has, near the nodal zone, a radially projecting collar coaxial with said tube, and in that at least one ultrasonic converter is disposed radially and fastened to said collar at its periphery, the frequency of said converter being equal to the vibration frequency of said collar and to the longitudinal vibration frequency of said tubular metal body.

Figure 1A:
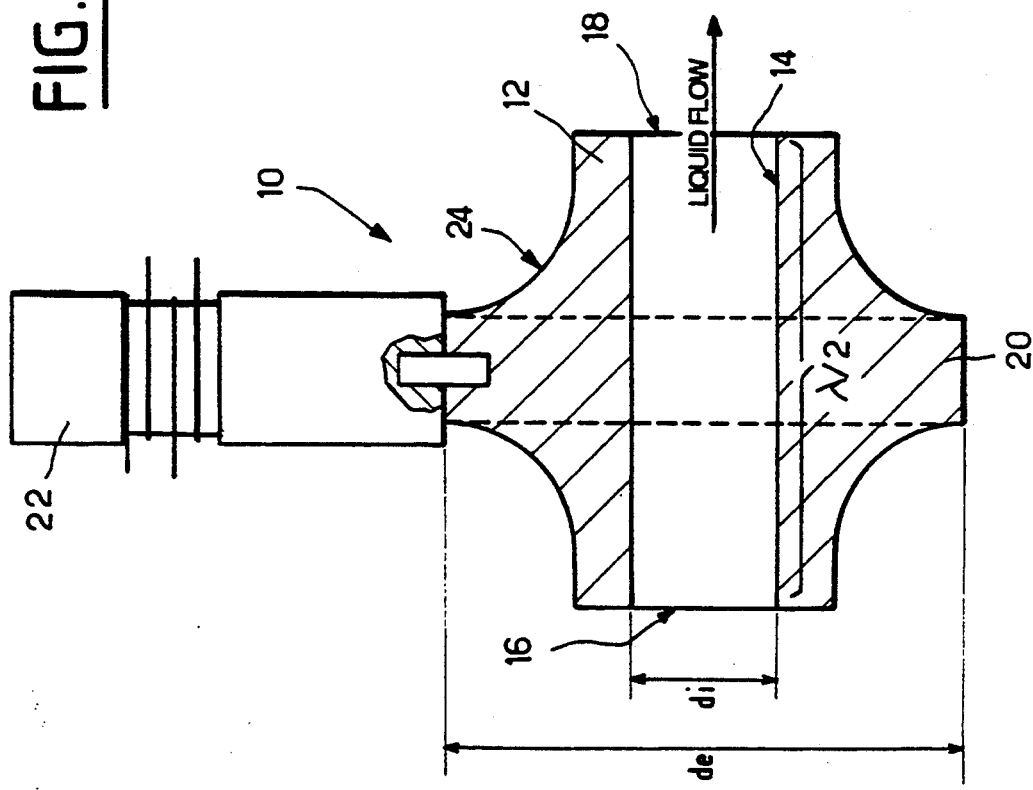
Figure 5:
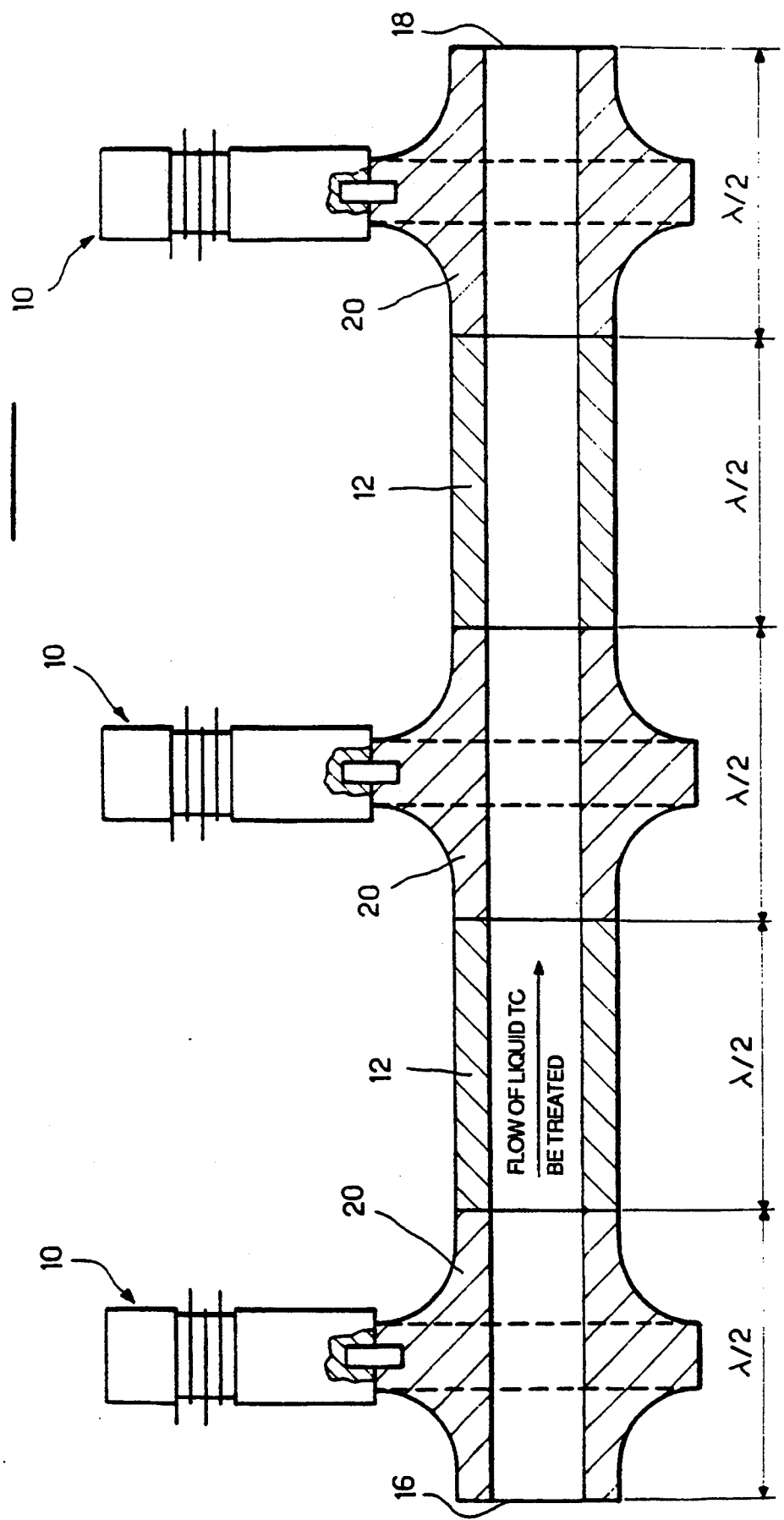
Figure 6B:
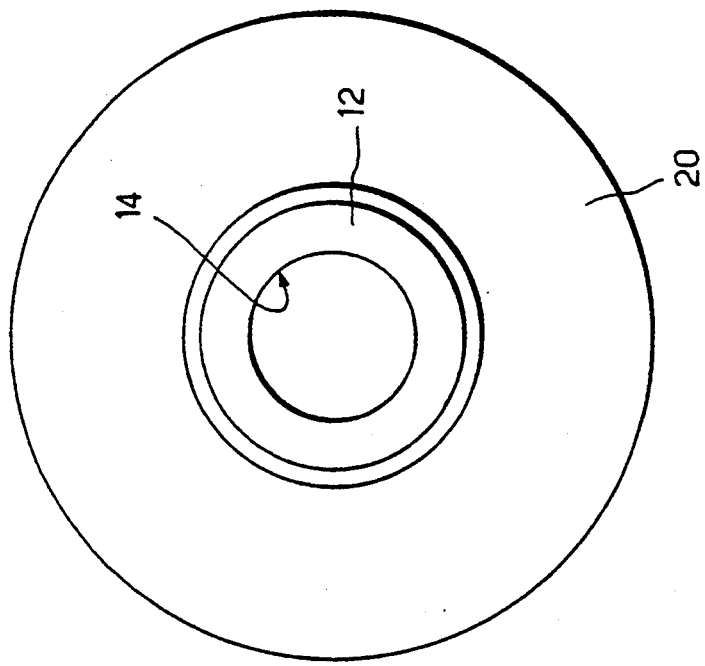
Figure 6A:
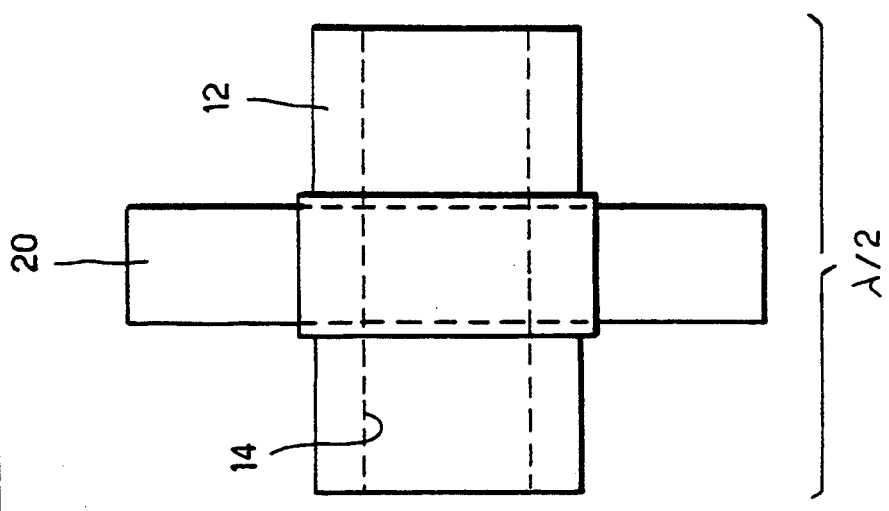
Figure 7:
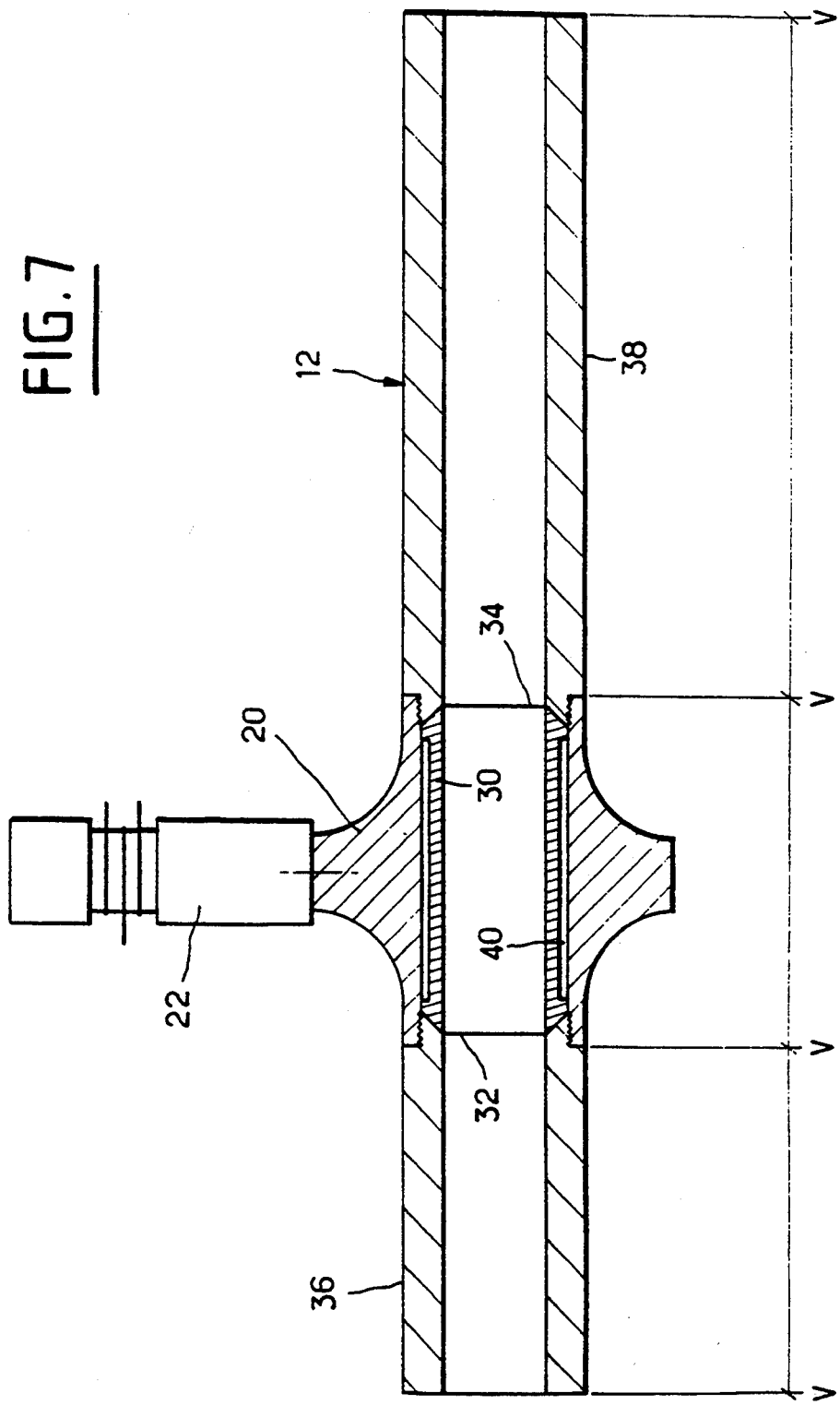

Other features and advantages of the present invention will emerge from the following detailed description given with reference to the appended drawings showing a number of specific embodiments, in which drawings:

FIG. 1A is a view in cross-section of one modular reactor unit in accordance with the invention, FIG. 1B shows an end view of the modular reactor unit from FIG. 1A, FIG. 2 shows an in-line multireactor comprising a plurality of modular reactor units in accordance with the invention associated with a single converter, FIG. 3 shows an in-line multireactor comprising a plurality of modular reactor units associated with three separate converters, FIG. 4 shows an in-line multireactor comprising a single modular unit with the tubular part of said reactor extended asymmetrically, FIG. 5 shows another embodiment of an in-line multireactor combining various modular units with a plurality of converters, and FIGS. 6A and 6B show a modular unit whose collar is attached to the tubular metal body, by means of a force fit, for example, FIG. 7 shows a modular unit employing an interior tubular member coupled to said unit in the vicinity of longitudinal maximum amplitude regions (stress nodes).

As shown in FIGS. 1A and 1B, which are respectively a side view and an end view of the modular reactor unit 10 in accordance with the invention, said unit mainly comprises three essential characteristic members. The unit 10 firstly comprises a tubular metal body 12 having a cylindrical interior surface 14 and a circular transverse cross-section. The tubular metal body 12 is open at both ends, i.e. its feed end 16 and its discharge end 18. The materials and/or reagents to be treated flow in the direction of the arrow from the end 16 to the end 18. The feed and discharge ends 16, 18 would be associated with feed and discharge pipes, possibly fitted with pumps. The remainder of the installation is not shown as it employs entirely conventional units well known to the man skilled in the art.

The modular unit 10 further comprises on the exterior surface of the tubular metal body 12, in the vicinity of the nodal zone of the latter, a collar 20 coaxial with said tube, said collar projecting radially outwards from the outside surface of the tubular body 12.

The modular unit 10 finally comprises at least one ultrasonic converter 22 which is disposed radially and fastened to said collar 20 at its periphery. In accordance with the present invention the frequency of said converter 22 is equal to the vibration frequency of said collar 20 and to the longitudinal vibration frequency of the tubular metal body 12.

In practise a conventional ultrasonic converter 22 is used, a piezoelectric excitation type converter, for example. This may be of the "Langevin triplet" type described in "High Intensity Ultrasonics" by B. Brown and J. E. Goodman.

In the specific embodiment described and shown in FIGS. 1A and 1B the coaxial collar 20 is machined in one piece with the tubular metal body 12. In this type of embodiment the collar 20 merges with the exterior surface of the tubular body 12 through rounded fillets 24. Note that in the embodiment described the length of the tubular metal body 12 is equal to one half-wavelength at the frequency used. Note also that the ultrasonic vibration frequency supplied by the emitter or the converter 22 is usually between 5 and 100 kHz. In this specific embodiment the length of the tubular metal body is strictly equal to one half-wavelength at the ultrasonic vibration frequency. Nevertheless, it is possible within the scope of the present invention to use a tubular metal part of greater length, extended on one or both sides of the coaxial collar 20 over a distance equal to an integer multiple of the half-wavelength at the output frequency, for example, this metal part being joined to the modular unit at longitudinal maximum amplitude regions (stress nodes) by means of screwthreads, a force fit, welding or like procedures, or machined in one piece with it.

It should be remembered that the inside and outside diameters of the collar 20 determine the radial frequency of the coaxial collar 20, the inside diameter of the collar 20 being equal to the inside diameter of the tubular metal body 12. On the other hand, the length of the tubular metal body 12, which is a multiple of half the wavelength, determines the longitudinal frequency of the reactor as a whole.

In the specific embodiment shown in FIGS. 1A and 1B a single converter or emitter 22 is used and this may be of the electrostrictive, magnetostrictive, electrocapacitive or (and more usually) piezo-electric type. The converter 22 is fixed to the periphery of the collar 20, preferably at a flat 26 adapted to ensure perfect contact between the emitter 22 and the collar 20. The mechanical coupling between these two units is advantageously provided by a pin or like member 28.

With reference to the ultrasonic vibration frequency delivered by the converter of the modular reactor unit 10 in accordance with the invention, the inside and outside diameters of $d_i$ and $d_e$ of the collar 20 may be conventionally determined by the man skilled in the art with reference to said vibration frequency delivered by the emitter. In the case of a collar 20 approximately 15 mm thick, for example, the inside and outside diameters of the collar are determined as a function of the vibration frequency F by the equation:

$$F = \frac{1.08 \cdot C}{\frac{d_i + d_e \cdot \pi}{2}}$$

where C represents the speed of sound in cm/s in the metal from which said collar 20 is made.

Consider, for example, an aluminum alloy collar excited by a 40 mm diameter 20 kHz piezo-electric emitter. In this case the collar has a thickness of 30 mm, an outside diameter of 130 mm and an inside diameter of 42 mm for the emitter output frequency of 20 kHz.

A reactor unit of this kind operates in the following manner. The vibration produced by the converter(s) 22 causes radial vibration of the collar 20 which causes longitudinal vibration of the tubular metal body 12 whose length is a multiple of half the wavelength. The phase in which the collar 20 is compressed corresponds to the phase in which the tubular body 12 expands longitudinally and expansion of the collar 20 corresponds to the phase in which the tubular body 12 is compressed longitudinally. To achieve this result the coaxial collar 20 must be near the nodal plane of the tubular body 12. The reactor in accordance with the invention uses the radial vibration of the inside diameter of the collar 20 to cause cavitation in any liquid to be treated flowing continuously through the interior of the tubular metal body 12.

Any liquid, gas, colloid or other material to be treated must be passed through the interior of the tubular metal body 12 of the reactor by conventional means (not shown).

FIG. 2 shows an ultrasonic reactor obtained by coupling in series a plurality of modular reactor units as shown in FIGS. 1A and 1B. The FIG. 2 embodiment comprises three modular units 10 forming an in-line multireactor but uses only one ultrasonic converter 22. An assembly of this kind may be of unitary construction or obtained by rigidly coupling said modular units at longitudinal maximum amplitude regions (stress nodes).

As shown in FIG. 3 it is also possible to obtain an in-line multireactor by associating a plurality of modular reactor units 10 coupled to a plurality of converters 22. In the specific embodiment described three complete modular units are employed each equipped with its converter 22. These complete units are disposed at the two ends and at the center of the tubular reactor. Note that between these complete half-wavelength modular units 10 there is disposed an assembly comprising a tubular metal body 12 also one half-wavelength long extended at its periphery by a coaxial collar 22. This is equivalent to an association of modular reactor units as previously described some of which have a length of one half-wavelength and others of which have a length of one wavelength.

The operation of this type of in-line reactor is identical to the operation of the modular units previously described. In the same phase of the vibratory movement there will thus be observed for the various associated elements simultaneous states, progressively, of compression and expansion.

When the linear ultrasonic reactor comprises a plurality of ultrasonic emitters or converters 22, the latter may advantageously be fed in parallel from the same generator. However, as a precaution the plurality of even ranked emitters should be inverted compared to the odd ranked emitters because of the phase inversion that occurs every half-wavelength.

The specific embodiment shown in FIG. 4 comprises a radial collar 20 which excites in series a length of tubular metal body extending the tubular part of the central modular element on either side of the latter. Note that the length of the tube on each side of the central modular unit is an integer multiple of half the wavelength. Said tubes may be screwed or force fitted to the modular unit at longitudinal maximum amplitude regions (stress nodes), for example. The arrangement need not be symmetrical. As shown in FIG. 4, in some intended applications it may be advantageous to provide a longer or shorter tubular area on the upstream or downstream side of the intense ultrasonic vibration area. In practise a number of half-wavelengths between 1 and 10 is usually chosen, depending on the material from which the reactor is made, the products to be treated and, of course, the nature and the conditions of the reaction occurring in the reactor. It may be advantageous, for example, as shown in FIG. 4, to provide a feed inlet relatively near the intense cavitation area, so that the energy required to initiate the reaction may be imparted quickly, the reaction then continuing in the downstream tubular part of the reactor, i.e. in an area where the ultrasonic cavitation is of lower amplitude and lower power.

Depending on the specific application intended, the man skilled in the art will choose a suitable length for said tubular metal body 12 equal to an integer number of half-wavelengths at the ultrasonic vibration frequency delivered by the converter(s) 22.

FIG. 5 shows a final embodiment in which a plurality of radial collars 20 are used to excite in series a length of tube which in this example is one half-wavelength long but could equally well comprise greater tube lengths equal to an integer number of half-wavelengths. The principle of operation is exactly the same.

FIG. 6 shows an alternative embodiment of a modular reactor unit in accordance with the invention. In this variant, rather than being machined in one piece, the coaxial collar 20 and the tubular metal body 12 are made separately. This enables the choice of a material having excellent acoustical properties, such as aluminum and/or titanium alloy, for the collar 20 and a different material having greater resistance to the erosion caused by ultrasonic cavitation for the metal tubular part 12 in which the liquid to be treated flows. The tubular part 12 might be made from a special steel such as stainless steel, for example. Furthermore, the interior surface 14 of the tubular reactor is advantageously provided with a protective layer to protect it against erosion due to cavitation, a ceramic coating, a hard metal coating or a combined ceramic/metal coating, for example. In the FIG. 6 embodiment the collar is attached to the tubular part by appropriate mechanical means providing a firm and homogeneous coupling. A rigid coupling is essential for the modular reactor unit in accordance with the invention and may be obtained, for example, by mechanical means such as screws, wedging or a force fit. Other non-mechanical means such as adhesive bonding, welding or the like may equally well be used.

FIG. 7 shows another embodiment of a modular reactor unit in accordance with the invention.

In this embodiment the modular reactor unit is adapted to receive inside it a tubular member 30 tuned to the frequency of the emitter 22, vibrating from the axial mode by clamping its two ends 32, 34 near longitudinal maximum amplitude regions (stress nodes) of said unit.

In this embodiment said tubular member 30 is clamped between two parts tuned to the emitter frequency, for example tubular metal bodies 36 and 38 as shown in FIG. 4.

The attached tubular member 30 advantageously has precision bearing surfaces (i.e. 45°) for perfect centering and good coupling with the members 36 and 38 clamping it at each end 32 and 34. Note, as shown in FIG. 7, a clearance 40 relative to the interior diameter of the modular unit to enable unrestricted radial expansion and compression of the tubular member 30 within which the fluid to be treated flows.

Modular reactor units in accordance with the invention may be used to treat all types of liquid, gas, colloid, etc flowing naturally or pumped through the interior of the reactors. Note that an exterior flow of liquid could be treated simultaneously by the cavitation caused by exterior vibration of the collars 20, i.e. two different flows of liquid could be treated simultaneously, one passing through the interior of the reactor and the other flowing over its exterior.

Reactors of this type have many industrial applications, for example:

activation of chemical reactions (Grignard, Barbier, etc),
de-agglomeration and washing of metal, ceramic and mineral powder,
treatment of ore,
wetting and dispersion of pigments, coloring agents,
accelerated dissolving of gases,
degassing,
homogenization,
wire cleaning,
emulsification, etc.

I claim:

1. Modular reactor unit for continuous ultrasonic treatment of materials and/or reagents characterized in that it comprises a tubular metal body (12) having a cylindrical interior (14) and a circular transverse cross-section open at a feed end (16) and a discharge end (18), in that the exterior surface of said tubular metal body has in the vicinity of the nodal zone a projecting radially collar (20) coaxial with said tube, and in that at least one ultrasonic converter (22) is disposed radially and attached to said collar at its periphery, the frequency of said converter (22) being equal to the frequency of vibration of said collar (20) and to the frequency of longitudinal vibration of said tubular metal body (12).

2. Modular reactor unit according to claim 1 characterized in that the length of said tubular metal body (12) is equal to an integer multiple of half the wavelength at the frequency of ultrasonic vibration emitted by said converter (22).

3. Modular reactor unit according to claim 1 characterized in that the frequency of ultrasonic vibration delivered by said converter (22) is between 5 and 100 kHz.

4. Modular reactor unit according to claim 1 characterized in that said ultrasonic converter (22) is fixed to the periphery of said collar (20) at a flat adapted to ensure perfect coupling of the converter (22) and the collar, the mechanical coupling being provided by a pin (28) or the like.

5. Modular reactor unit according to claim 1 characterized in that said collar (20) is machined in one piece with the tubular metal body (12).

6. Modular reactor unit according to claim 1 characterized in that said collar (20) is attached to said tubular metal body (12) by any means providing a rigid coupling.

7. Modular reactor unit according to claim 6 characterized in that said collar (20) is made from a metal having good acoustical properties such as aluminum and/or titanium alloy and in that said tubular metal body (12) is made from a metal having a good resistance to erosion caused by cavitation such as stainless steel.

8. Modular reactor unit according to claim 1 characterized in that the interior surface (14) of the tubular reactor has a ceramic, hard metal or combined ceramic/metal coating to protect it against erosion by cavitation.

9. Modular reactor unit according to claim 1 characterized in that a tubular member (30) is attached to the interior of said unit by clamping means in the vicinity of longitudinal maximum amplitude regions of said unit.

10. Ultrasonic reactor characterized in that it comprises a series coupling of a plurality of modular reactor units (10) according to any one claim 1 to create an in-line multireactor.

11. Ultrasonic reactor according to claim 10 characterized in that it comprises a plurality of converters (22) fed in parallel by the same generator.

* * * * *